US008859196B2

(12) United States Patent
Trulson et al.

(10) Patent No.: US 8,859,196 B2
(45) Date of Patent: *Oct. 14, 2014

(54) ANTIREFLECTIVE COATINGS FOR HIGH-RESOLUTION PHOTOLITHOGRAPHIC SYNTHESIS OF DNA ARRAYS

(75) Inventors: Mark O. Trulson, San Jose, CA (US); Glenn H. McGall, Palo Alto, CA (US); Bei-Shen Sywe, Cupertino, CA (US); Lisa T. Kajisa, Palo Alto, CA (US); Dana Truong, Sacramento, CA (US); Richard P. Rava, Redwood City, CA (US); Martin J. Goldberg, Saratoga, CA (US)

(73) Assignee: Affymetrix, Inc., Santa Clara, CA (US)

( * ) Notice: Subject to any disclaimer, the term of this patent is extended or adjusted under 35 U.S.C. 154(b) by 215 days.

This patent is subject to a terminal disclaimer.

(21) Appl. No.: 13/275,521

(22) Filed: Oct. 18, 2011

(65) Prior Publication Data

US 2012/0035083 A1 Feb. 9, 2012

Related U.S. Application Data

(60) Continuation of application No. 12/832,781, filed on Jul. 8, 2010, now Pat. No. 8,114,584, which is a division of application No. 12/014,879, filed on Jan. 16, 2008, now Pat. No. 7,790,389, which is a division of application No. 10/177,169, filed on Jun. 20, 2002, now Pat. No. 7,332,273.

(51) Int. Cl.

| C12Q 1/00 | (2006.01) |
| G03F 7/09 | (2006.01) |
| B82Y 30/00 | (2011.01) |
| C12Q 1/68 | (2006.01) |
| B01J 19/00 | (2006.01) |
| C40B 40/06 | (2006.01) |

(52) U.S. Cl.
CPC .............. B82Y 30/00 (2013.01); G03F 7/091 (2013.01); *B01J 2219/00612* (2013.01); *B01J 2219/00722* (2013.01); *B01J 2219/00608* (2013.01); C12Q 1/6837 (2013.01); *B01J 2219/00626* (2013.01); *B01J 2219/0061* (2013.01); *C40B 40/06* (2013.01); *B01J 2219/00711* (2013.01); *B01J 2219/00637* (2013.01); B01J 19/0046 (2013.01)
USPC .......................................................... 435/4

(58) Field of Classification Search
None
See application file for complete search history.

(56) References Cited

U.S. PATENT DOCUMENTS

| 4,839,553 A | 6/1989 | Mellor |
| 5,143,854 A | 9/1992 | Pirrung et al. |
| 5,384,261 A | 1/1995 | Winkler et al. |
| 5,412,087 A | 5/1995 | McGall et al. |
| 5,418,136 A | 5/1995 | Miller et al. |
| 5,424,186 A | 6/1995 | Fodor et al. |
| 5,489,678 A | 2/1996 | Fodor et al. |
| 5,545,531 A | 8/1996 | Rava et al. |
| 5,550,063 A | 8/1996 | Bogart |
| 5,552,272 A | 9/1996 | Bogart |
| 5,576,220 A | 11/1996 | Hudson et al. |
| 5,629,214 A | 5/1997 | Crosby |
| 5,631,171 A | 5/1997 | Sandstrom et al. |
| 5,639,671 A | 6/1997 | Bogart et al. |
| 5,677,195 A | 10/1997 | Winkler et al. |
| 5,869,272 A | 2/1999 | Bogart et al. |
| 5,955,377 A | 9/1999 | Maul et al. |
| 5,959,098 A * | 9/1999 | Goldberg et al. ............ 536/25.3 |
| 6,057,424 A | 5/2000 | Vail |
| 6,060,237 A | 5/2000 | Nygren et al. |
| 6,235,471 B1 | 5/2001 | Knapp et al. |
| 6,261,782 B1 | 7/2001 | Lizardi et al. |
| 6,262,216 B1 | 7/2001 | McGall |
| 6,355,429 B1 | 3/2002 | Nygren et al. |
| 6,368,808 B2 | 4/2002 | Sato et al. |
| 6,486,287 B2 | 11/2002 | McGall et al. |
| 6,506,594 B1 | 1/2003 | Barany et al. |
| 6,506,716 B1 | 1/2003 | Delplancke et al. |
| 6,528,264 B1 | 3/2003 | Pal et al. |
| 6,569,382 B1 | 5/2003 | Edman et al. |
| 6,569,598 B2 | 5/2003 | Zebala |
| 6,573,369 B2 * | 6/2003 | Henderson et al. .......... 536/23.1 |
| 6,586,238 B1 | 7/2003 | Matulic-Adamic et al. |
| 6,589,779 B1 | 7/2003 | McDevitt et al. |
| 6,602,702 B1 | 8/2003 | McDevitt et al. |
| 6,605,363 B2 | 8/2003 | Ho et al. |
| 6,610,142 B1 | 8/2003 | Takayama et al. |
| 6,610,645 B2 | 8/2003 | Pancheri et al. |

(Continued)

FOREIGN PATENT DOCUMENTS

| EP | 1540005 | 6/2005 |
| JP | 07-239947 | 9/1995 |
| JP | 10-288616 | 10/1998 |
| WO | WO 91/04491 | 4/1991 |

*Primary Examiner* — Ann Lam
(74) *Attorney, Agent, or Firm* — Banner & Witcoff, Ltd.

(57) ABSTRACT

The present invention provides an array of polymers and methods of forming arrays of polymers by providing a substrate having a first layer including one or more dielectric coatings on a solid support and a second layer including a plurality of polymers disposed on the first layer. The invention also provides methods for forming an array of polymers on a substrate using light-directed synthesis by providing a substrate having a first layer including one or more dielectric coatings on a solid support, derivatizing the first layer by contacting the first layer with a silanation reagent, and a second layer disposed on said first layer wherein the second layer includes functional groups protected with a photolabile protecting group.

33 Claims, 6 Drawing Sheets

(56) References Cited

U.S. PATENT DOCUMENTS

| | | |
|---|---|---|
| 6,649,403 B1 | 11/2003 | McDevitt et al. |
| 6,652,808 B1 | 11/2003 | Heller et al. |
| 6,656,428 B1 | 12/2003 | Clark et al. |
| 6,660,338 B1 | 12/2003 | Hargreaves |
| 6,660,517 B1 | 12/2003 | Wilding et al. |
| 6,680,206 B1 | 1/2004 | McDevitt et al. |
| 6,682,924 B1 | 1/2004 | Sierkstra et al. |
| 6,706,473 B1 | 3/2004 | Edman et al. |
| 6,713,298 B2 | 3/2004 | McDevitt et al. |
| 6,731,831 B2 | 5/2004 | Tu |
| 6,733,894 B2 | 5/2004 | Ho et al. |
| 7,153,682 B2 | 12/2006 | Charych et al. |
| 7,195,872 B2 | 3/2007 | Agrawal et al. |
| 7,332,273 B2 * | 2/2008 | Trulson et al. ............... 435/6.11 |
| 7,790,389 B2 * | 9/2010 | Trulson et al. ............... 435/6.11 |
| 8,114,584 B2 * | 2/2012 | Trulson et al. ................... 435/4 |
| 2007/0154946 A1 | 7/2007 | Rajasekaran et al. |
| 2007/0275411 A1 | 11/2007 | McGall |
| 2009/0215652 A1 | 8/2009 | McGall et al. |

* cited by examiner

FIGURE 3
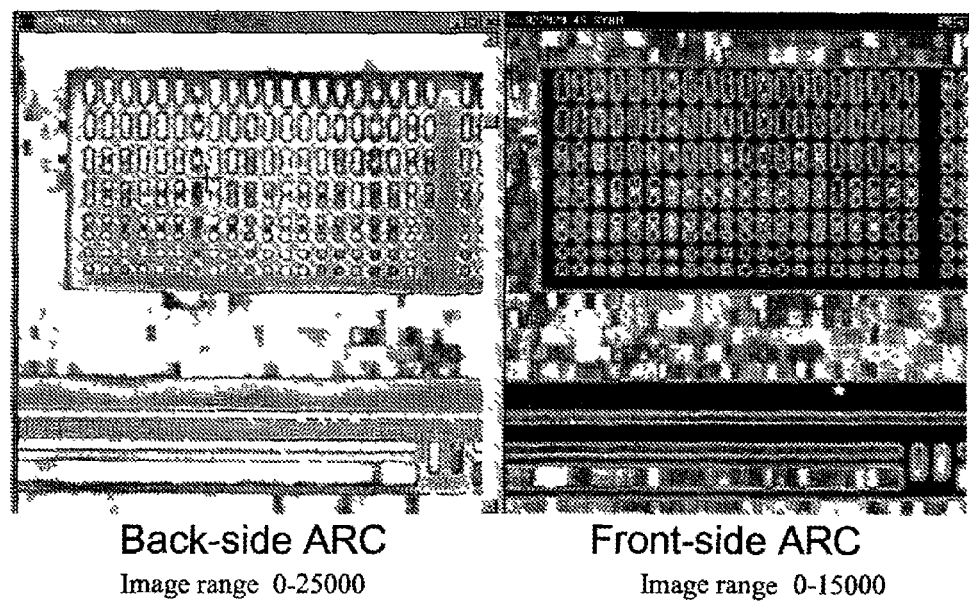
Back-side ARC  
Image range 0-25000
Front-side ARC  
Image range 0-15000
FIGURE 3A
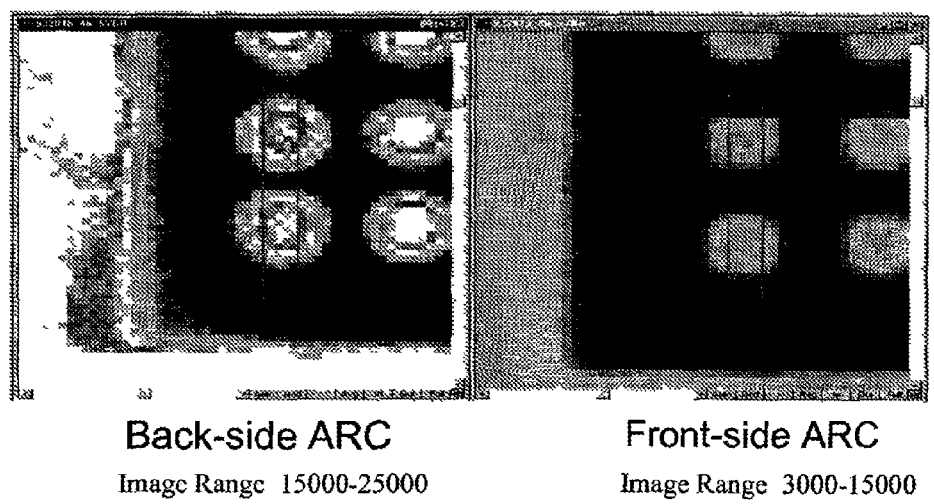
Back-side ARC  
Image Range 15000-25000
Front-side ARC  
Image Range 3000-15000
FIGURE 3B Back-side ARC | Front-side ARC Back-side ARC         Front-side ARC

ANTIREFLECTIVE COATINGS FOR HIGH-RESOLUTION PHOTOLITHOGRAPHIC SYNTHESIS OF DNA ARRAYS

CROSS REFERENCE TO RELATED APPLICATIONS

This application is a continuation of U.S. patent application No. 12/832,781, filed Jul. 8, 2010 now U.S. Pat No. 8,114,584; which was a division of U.S. patent application No. 12/014,879, filed Jan. 16, 2008, which issued as U.S. Pat. No. 7,790,389, and which was a division of U.S. patent application No. 10/177,169filed Jun. 20, 2002, which issued as U.S. Pat. No. 7,332,273. Each of these is incorporated by reference herein in their entirety.

FIELD OF INVENTION

This invention relates to improved methods for high-resolution photolithographic synthesis of oligonucleotide arrays. The improved methods relate to an improved substrate coating and silanation process that provides higher photolithographic contrast resolution, thereby improving the quality and information density on arrays.

BACKGROUND OF THE INVENTION

Methods have been developed for producing large arrays of polymer sequences on solid substrates. These large arrays of polymer sequences have wide ranging applications and are of substantial importance to the pharmaceutical, biotechnology and medical industries. For example, the arrays may be used in screening large numbers of molecules for biological activity, i.e., receptor binding capability. Alternatively, arrays of oligonucleotide probes can be used to identify mutations in known sequences, as well as in methods for de novo sequencing of target nucleic acids.

Of particular note, is the pioneering work described in U.S. Pat. No. 5,143,854 (Pirrung et al.) and PCT Application No. 92/10092 disclose improved methods of molecular synthesis using light directed techniques. According to these methods, light is directed to selected regions of a substrate to remove protecting groups from the selected regions of the substrate. Thereafter, selected molecules are coupled to the substrate, followed by additional irradiation and coupling steps. By activating selected regions of the substrate and coupling selected monomers in precise order, one can synthesize an array of molecules having any number of different sequences, where each different sequence is in a distinct, known location on the surface of the substrate. These arrays clearly embody the next step in solid phase synthesis of polymeric molecules generally, and polypeptides and oligonucleotides, specifically.

U.S. Pat. No. 5,959,098 provides processes for the efficient, large scale preparation of arrays of polymer sequences wherein each array includes a plurality of different, positionally distinct polymer sequences having known monomer sequences. In one embodiment, it provides a substrate having a first surface coated with functional groups protected with a photolabile protecting group, and a second surface on the backside having a layer that includes one or more of an index matching compound, a light absorbing compound and an antireflective compound. During the exposure step, certain amount of the light passing through the substrate is still reflected back from the glass-polymer interface onto the front (synthesis) side of the substrate, due to a mismatch in the refractive indices of the two materials.

SUMMARY OF THE INVENTION

The present invention generally provides novel processes for the efficient preparation of arrays of polymer sequences wherein each array includes a plurality of different, positionally distinct polymer sequences having known monomer sequences. In one embodiment, the present invention provides methods for forming polymer arrays by providing a substrate having a first layer on a solid support and a second layer disposed on the first layer. The first layer includes a dielectric coating with stack of dielectric materials possessing antireflective, index matching and/or light absorbing properties. The second layer includes a plurality of polymers disposed on said first layer. The method then provides for the sequential activation and coupling of monomers in different selected regions of the surface of the substrate to form a plurality of different polymer sequences in different known locations on the surface of the substrate, by directing an activation radiation at the surface of the substrate.

In another embodiment, the present invention provides methods for forming an array of polymers on a substrate using light-directed synthesis by providing a substrate having a first layer on a solid support, said first layer including one or more dielectric coatings; derivatizing said first layer by contacting said first layer with silanation reagents, and a second layer disposed on said first layer wherein said second layer includes functional groups protected with a photolabile protecting group. The method then provides for activating first selected regions on said surface of said substrate by removing said protecting groups from said functional groups in said first selected regions; coupling a first monomer to said functional groups in said first selected regions; activating second selected regions on said surface of said substrate by removing said protecting groups from said functional groups in said second selected regions; coupling a second monomer to said functional groups in said second selected regions; and repeating said activating and coupling steps to form a plurality of different polymer sequences, each of said different polymer sequences being coupled to said surface of said substrate in a different known location.

The present invention also provides for an array of polymers on a surface of a substrate, comprising a first layer on a solid support, said first layer including one or more stacks of dielectric materials on said solid support and a second layer including a plurality of polymers disposed on said first layer.

BRIEF DESCRIPTION OF THE DRAWINGS

FIG. 3. Back-side ARC and front-side ARC wafers were compared to evaluate their photolithographic contrast. FIG. 3(a) shows a back-side ARC v front-side ARC wafers, 12 micron feature size scanned at 1.5 micron pixel size, Sybr Green stained images, Dev-Val Mask Set. FIG. 3(b) shows the magnified bottom left section of FIG. 3(a).

DETAILED DESCRIPTION OF THE INVENTION

Figure 1:
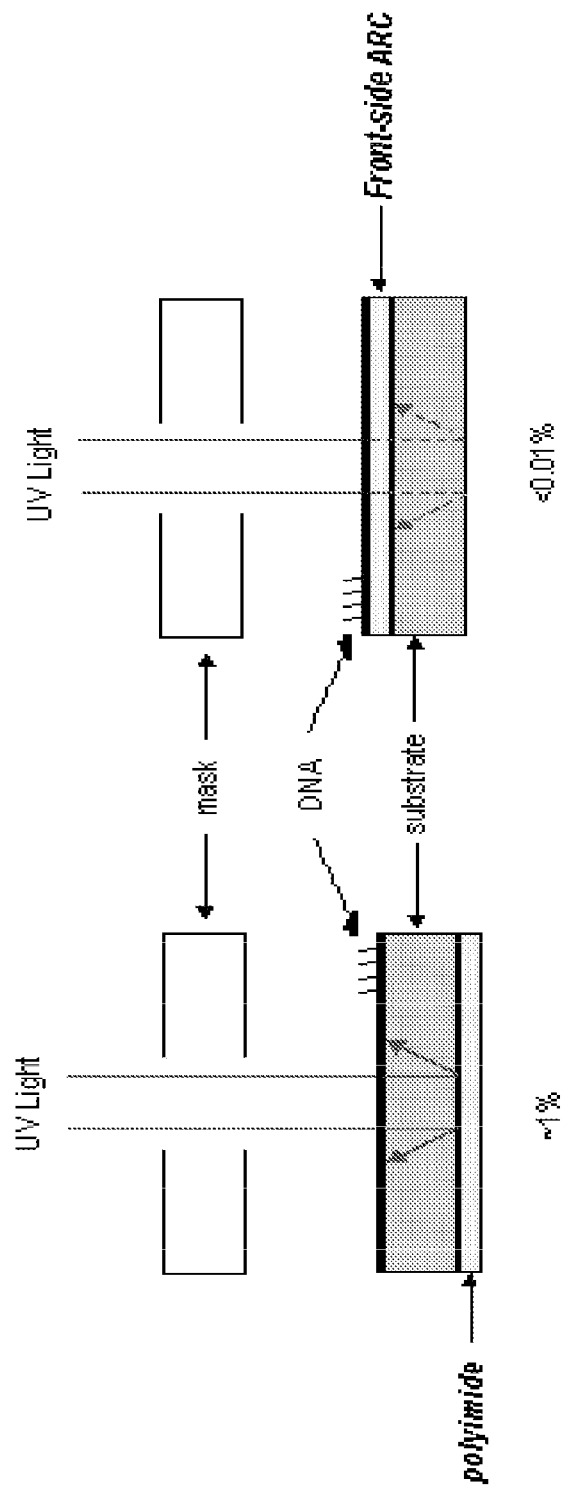
FIG. 1. Schematic diagrams showing back-side antireflective coating (ARC) and front-side ARC on fused silica substrates.

The present invention has many preferred embodiments and relies on many patents, applications and other references for details known to those of the art. Therefore, when a patent, application, or other reference is cited or repeated below, it should be understood that it is incorporated by reference in its entirety for all purposes as well as for the proposition that is recited.

As used in this application, the singular form "a," "an," and "the" include plural references unless the context clearly dictates otherwise. For example, the term "an agent" includes a plurality of agents, including mixtures thereof.

An individual is not limited to a human being but may also be other organisms including but not limited to mammals, plants, bacteria, or cells derived from any of the above.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

I. Synthesis of DNA Arrays

General methods for the solid phase synthesis of a variety of polymer types have been previously described. Methods of synthesizing arrays of large numbers of polymer sequences, including oligonucleotides and peptides, on a single substrate have also been described. See U.S. Pat. Nos. 5,143,854 and 5,384,261 and Published PCT Application No WO 92/10092, each of which is incorporated herein by reference in its entirety for all purposes.

As described previously, the synthesis of oligonucleotides on the surface of a substrate may be carried out using light directed methods as described in, e.g., U.S. Pat. Nos. 5,143,854 and 5,384,261 and Published PCT Application No WO 92/10092, or mechanical synthesis methods as described in U.S. Pat. Nos. 5,384,261, 6,040,193 and Published PCT Application No. 93/09668, each of which is incorporated herein by reference. Preferably, synthesis is carried out using light-directed synthesis methods. In particular, these light-directed or photolithographic synthesis methods involve a photolysis step and a chemistry step. The substrate surface, prepared as described herein comprises functional groups on its surface. These functional groups are protected by photolabile protecting groups ("photoprotected"). During the photolysis step, portions of the surface of the substrate are exposed to light or other activators to activate the functional groups within those portions, i.e., to remove photoprotecting groups. The substrate is then subjected to a chemistry step in which chemical monomers that are photoprotected at least one functional group are then contacted with the surface of the substrate. These monomers bind to the activated portion of the substrate through an unprotected functional group.

Subsequent activation and coupling steps couple monomers to other preselected regions, which may overlap with all or part of the first region. The activation and coupling sequence at each region on the substrate determines the sequence of the polymer synthesized thereon. In particular, light is shown through the photolithographic masks which are designed and selected to expose and thereby activate a first particular preselected portion of the substrate. Monomers are then coupled to all or part of this portion of the substrate. The masks used and monomers coupled in each step can be selected to produce arrays of polymers having a range of desired sequences, each sequence being coupled to a distinct spatial location on the substrate which location also dictates the polymer's sequence. The photolysis steps and chemistry steps are repeated until the desired sequences have been synthesized upon the surface of the substrate.

Basic photolithographic methods are also described in U.S. Pat. Nos. 5,143,854, 5,489,678 and Published PCT Application No. WO 94/10128 each of which is incorporated herein by reference in its entirety for all purposes. The surface of a substrate, modified with photosensitive protecting groups is illuminated through a photolithographic mask, yielding reactive hydroxyl groups in the illuminated regions. A selected nucleotide, typically in the form of a 3'-O-phosphoramidite-activated deoxynucleoside (protected at the 5' hydroxyl with a photosensitive protecting group), is then presented to the surface and coupling occurs at the sites that were exposed to light. Following capping and oxidation, the substrate is rinsed and the surface is illuminated through a second mask, to expose additional hydroxyl groups for coupling. A second selected nucleotide (e.g., 5'-protected, 3'-O-phosphoramidite-activated deoxynucleoside) is presented to the surface. The selective deprotection and coupling cycles are repeated until the desired set of products is obtained. Pease et al., *Proc. Natl. Acad. Sci.* (1994) 91:5022-5026. Since photolithography is used, the process can be readily miniaturized to generate high density arrays of oligonucleotide probes. Furthermore, the sequence of the oligonucleotides at each site is known.

In one preferred embodiment, an array of polymers was synthesized on a substrate using light-directed synthesis by providing a substrate having a first layer on a solid support, said first layer including one or more stacks of dielectric materials; derivatizing said first layer by contacting said first layer with silanation reagents, and a second layer disposed on said first layer wherein said second layer includes functional groups protected with a photolabile protecting group. The method then provides for activating first selected regions on said surface of said substrate by removing said protecting groups from said functional groups in said first selected regions; coupling a first monomer to said functional groups in said first selected regions; activating second selected regions on said surface of said substrate by removing said protecting groups from said functional groups in said second selected regions; coupling a second monomer to said functional groups in said second selected regions; and repeating said activating and coupling steps to form a plurality of different polymer sequences, each of said different polymer sequences being coupled to said surface of said substrate in a different known location.

Using the above described methods, arrays may be prepared having all polymer sequences of a given length which are composed of a basis set of monomers. Such an array of oligonucleotides, made up of the basis set of four nucleotides, for example, would contain up to $4^n$ oligonucleotides on its surface, where n is the desired length of the oligonucleotide probe. For an array of 8mer or 10mer oligonucleotides, such arrays could have upwards of about 65,536 and 1,048,576 different oligonucleotides respectively. Generally, where it is desired to produce arrays having all possible polymers of length n, a simple binary masking strategy can be used, as described in U.S. Pat. No. 5,143,854.

Alternate masking strategies can produce arrays of probes which contain a subset of polymer sequences, i.e., polymers having a given subsequence of monomers, but are systematically substituted at each position with each member of the basis set of monomers. In the context of oligonucleotide probes, these alternate synthesis strategies may be used to lay down or "tile" a range of probes that are complementary to, and span the length of a given known nucleic acid segment. The tiling strategy will also include substitution of one or more individual positions within the sequence of each of the probe groups with each member of the basis set of nucleotides. These positions are termed "interrogation positions." By reading the hybridization pattern of the target nucleic acid, one can determine if and where any mutations lie in the sequence, and also determine what the specific mutation is by identifying which base is contained within the interogation position. Tiling methods and strategies are discussed in substantial detail in U.S. Pat. No. 6,027,880 and incorporated herein by reference in its entirety for all purposes.

Tiled arrays may be used for a variety of applications, such as identifying mutations within a known oligonucleotide sequence or "target". Specifically, the probes on the array will have a subsequence which is complementary to a known nucleic acid sequence, but wherein at least one position in that sequence has been systematically substituted with the other three nucleotides.

II. Substrate Preparation

The term "substrate" refers to a material having a rigid or semi-rigid surface onto which the polymers are placed, attached or bound, for example. A monomer or building block is a member of the set of smaller molecules which can be joined together to form a larger molecule or polymer. The set of monomers includes but is not restricted to, for example, the set of common L-amino acids, the set of D-amino acids, the set of natural or synthetic amino acids, the set of nucleotides (both ribonucleotides and deoxyribonucleotides, natural and unnatural) and the set of pentoses and hexoses. As used herein, monomer refers to any member of a basis set for synthesis of a larger molecule. A selected set of monomers forms a basis set of monomers. For example, the basis set of nucleotides includes A, T (or U), G and C. In another example, dimers of the 20 naturally occurring L-amino acids form a basis set of 400 monomers for synthesis of polypeptides. Different basis sets of monomers may be used in any of the successive steps in the synthesis of a polymer. Furthermore, each of the sets may include protected members which are modified after synthesis.

In many embodiments, at least one surface of the substrate will be substantially flat or planar, although in some embodiments it may be desirable to physically separate synthesis regions for different polymers with, for example, wells, raised regions, etched trenches, or the like. According to other embodiments, small beads may be provided on the surface which may be released upon completion of the synthesis. Preferred substrates generally comprise planar crystalline substrates such as silica based substrates (e.g. glass, quartz, or the like), or crystalline substrates used in, e.g., the semiconductor and microprocessor industries, such as silicon, gallium arsenide and the like. These substrates are generally resistant to the variety of synthesis and analysis conditions to which they may be subjected. Particularly preferred substrates will be transparent to allow the photolithographic exposure of the substrate from either direction. See U.S. Pat. No. 5,143,854 for other substrates.

Silica aerogels may also be used as substrates. Aerogel substrates may be used as free standing substrates or as a surface coating for another rigid substrate. Aerogel substrates provide the advantage of large surface area for polymer synthesis, e.g., 400 to 1000 m$^2$/gm, or a total useful surface area of 100 to 1000 cm$^2$ for a 1 cm$^2$ piece of aerogel substrate. Such aerogel substrates may generally be prepared by methods known in the art, e.g., the base catalyzed polymerization of (MeO)$_4$Si or (EtO)$_4$Si in ethanol/water solution at room temperature. Porosity may be adjusted by altering reaction condition by methods known in the art.

Individual planar substrates generally exist as wafers which can have varied dimensions. The term "wafer" generally refers to a substantially flat sample of substrate from which a plurality of individual arrays or chips may be fabricated. The term "array" or "chip" is used to refer to the final product of the individual array of polymer sequences, having a plurality of different positionally distinct polymer sequences coupled to the surface of the substrate. The size of a substrate wafer is generally defined by the number and nature of arrays that will be produced from the wafer. For example, more complex arrays, e.g., arrays having all possible polymer sequences produced from a basis set of monomers and having a given length, will generally utilize larger areas and thus employ larger substrates, whereas simpler arrays may employ smaller surface areas, and thus, less substrate.

Typically, the substrate wafer will range in size of from about 1"×1" to about 12"×12", and will have a thickness of from about 0.5 mm to about 5 mm. Individual substrate segments which include the individual arrays, or in some cases a desired collection of arrays, are typically much smaller than the wafers, measuring from about 0.2 cm×0.2 cm to about 5 cm×5 cm. In particularly preferred aspects, the substrate wafer is about 5"×5" whereas the substrate segment is approximately 1.28 cm×1.28 cm. Although a wafer can be used to fabricate a single large substrate segment, typically, a large number of substrate segments will be prepared from a single wafer. For example, a wafer that is 5"×5" can be used to fabricate upwards of 49 separate 1.28 cm×1.28 cm substrate segments. The number of segments prepared from a single wafer will generally vary depending upon the complexity of the array, and the desired feature size.

III. Antireflective Coatings

A. Back-side Coating

As described above, photolithographic methods are used to activate selected regions on the surface of the substrate. Specifically, functional groups on the surface of the substrate or present on growing polymers on the surface of the substrate, are protected with photolabile protecting groups. Activation of selected regions of the substrate is carried out by exposing selected regions of the substrate surface to activation radiation, e.g., light within the effective wavelength range. Selective exposure is typically carried out by shining a light source through a photolithographic mask.

A feature is defined as a selected region on a surface of a substrate in which a given polymer sequence is designed to be contained. Thus, where any array contains, e.g., 100,000 different positionally distinct polymer sequences on a single substrate, there will be 100,000 features. An edge is defined as a boundary between two features on a surface of a substrate. The sharpness of this edge, in terms of reduced bleed over from one feature to another, is termed the resolution "contrast" of the two features. Because the individual feature sizes on the surface of the substrate prepared according to the processes described herein can typically range as low as 1-10 μm on a side, the effects of diffracted, reflected or scattered light at the surface of the substrate can have significant effects upon the ability to expose and activate features of this size. One method of reducing the potentially deleterious effects of diffraction, refraction and scattering of the photolytic light source is by applying a coating layer to the back-side of the substrate, i.e., to the non-synthesis surface of the substrate. The coating layer is typically applied after the substrate preparation process, but prior to derivatization. This coating is typically selected to perform one or more of the following functions: (1) match the refractive index of the substrate to prevent reflection of light at the substrate/coating interface which may interfere with the photolysis; and (2) absorb light at the wavelength of light used during photolysis, to prevent back reflection at the coating/air or fixture interface which may also interfere with photolysis.

Typically, suitable coating materials may be selected from a number of suitable materials which have a refractive index approximately equal to that of the substrate and/or absorb light at the appropriate wavelength. In particular, index matching coatings are typically selected to have a refractive index that is within at about 25% that of the substrate, more preferably within about 10% that of the substrate, and more preferably within about 5%. Similarly, light absorbing coatings are typically selected whereby light at the photolytic wavelength is absorbed, which in preferred aspects is light in the ultraviolet range, e.g., between 280 nm and 400 nm. Light absorbing coatings and index matching coatings may be combined to provide combined protection against refraction and reflection, or a single coating material may be selected which possesses both of the desired properties.

Preferred polymers will typically be selected to be compatible with the various reaction conditions which would be encountered during the synthesis process, e.g., insoluble in and non-reactive with synthesis reagents, and resistant to the mechanical forces involved in handling and manipulating the substrate, throughout the synthesis process. Additionally, preferred coating materials are easily removable upon completion of the synthesis process, e.g., in the final deprotection step or in a final coating removal step.

Examples of suitable coating materials include antireflective coatings that are well known in the art and generally commercially available, e.g., magnesium fluoride compounds, which are light-absorbing in the desired wavelength range, polymethylmethacrylate coatings (PMMA), which have a refractive index comparable to glass substrates, and polyimide coatings which are both light-absorbing in the desired wavelength range, and have a refractive index close to that of a glass substrate. See Handbook of Optics, Fundamentals, Techniques and Design, Second Edition, Michael Bass (Editor in Chief), McGraw-Hill, Inc. (1995) for additional examples.

Application of the coating materials may be carried out by a variety of methods, including, e.g., vapor deposition, spray application, and the like. In preferred aspects, the coating solution will be applied to the substrate using a spin-coating method. Typically, this involves spinning the substrate during deposition of the coating solution on the substrate surface that is to be coated. The spinning substrate results in spreading of the coating solution radially outward on the surface of the substrate. Other methods of coating can be found in, for example, Thin-film Optical Filters, Third Edition, H. Angus Macleod, Institute of Physics Publishing (2001). Such methods are well known in the art. For example, see Laser Focus World, 2002 Buyers Guide, Vol 38 Issue 1, Section 7: Finished Optics and Coatings, pp 445-582.

Application of the coating material using the spin-coating process usually employs a two-speed spinning of the substrate. The application of the coating material to the surface of the substrate and initial spreading of the coating solution are usually carried out at low rotational speeds and for relatively short duration. For example, to apply 1 ml of a 12% solids w/v polymer coating solution to a 4.3"×4.3" substrate, initial spreading is carried out at 500 r.p.m. for 10 seconds. Elimination of excess polymer solution and evening of the polymer layer are carried out at higher rotational speeds and for substantially longer durations. For example in the application described above, the second spinning step is carried out at approximately 3000 r.p.m. for 30 seconds. It will be understood by those of skill in the art, that the above described parameters for spin-coating can be varied within the scope of the present invention. For example, where higher concentration (w/v) polymer solutions are used, it may be desirable to increase one or both rotational speeds, as well as the time at a given speed. Similarly, where the polymer concentration in the polymer solution is reduced, lower speeds and shorter spin times may be used.

Following application, the polymer coating can be cured on the surface of the substrate. Curing is typically carried out by heating the coated substrate. In preferred processes, the curing process involves a two-step heating process. The first step involves a "soft-bake" heating of the coated substrate to initially cure the polymer coating. This soft-bake step typically takes place at relatively low temperatures for relatively short periods, i.e., 85° C. for 5 minutes. The second step of the curing process is a final curing of the polymer coating which is typically carried out at higher temperatures for longer periods, i.e., 220-360° C., for approximately 60 minutes. In preferred aspects, a polymer coating applied to the back side of the substrate will be from about 1 to about 50 μm thick, and more preferably, from about 5 to about 20 μm thick, with polymer coating of about 5 μm thick being most preferred. After coating, the substrate is then subjected to derivitization, rinsing and baking, as described in U.S. Pat. No. 5,959,098, which is incorporated herein by reference in its entirety for all purposes.

B. Front-side Coating

Photolithographic masks used during the photolysis step typically include transparent regions and opaque regions, for exposing only selected portions of the substrate during a given photolysis step. Typically, the masks are fabricated from glass that has been coated with a light-reflective or absorptive material, e.g., a chrome layer. The light-reflective or absorptive layer is etched to provide the transparent regions of the mask. These transparent regions correspond to the regions to be exposed on the surface of the substrate when light is shown through the mask.

In general, it is desirable to produce arrays with smaller feature sizes, allowing the incorporation of larger amounts of information in a smaller substrate area, allowing interrogation of larger samples, more definitive results from an interrogation and greater possibility of miniaturization. Alternatively, by reducing feature size, one can obtain a larger number of arrays, each having a given number of features, from a single substrate wafer. The result is substantially higher product yields for a given process.

In seeking to reduce feature size, it is important to maximize the contrast between the regions of the substrate exposed to light during a given photolysis step, and those regions which remain dark or are not exposed. The sharpness of this edge, in terms of reduced bleed over from one feature to another, is termed the "contrast" between the two features.

One cause of reduced contrast is "bleed-over" from exposed regions to non-exposed regions during a particular photolysis step. The root cause of light bleeding is poor light collimation. With the back-side polyimide coating, about 1.3% of the light is reflected from the interface of the coating, a result of the imperfect match of the refractive index between the fused silica and the back-side coating, as indicated in FIG. 1. By providing a front-side coating, the reflection of light of backside of wafer is substantially reduced, for example, to as low as less than 0.05%, 0.01%, 0.005% or more. Thus having a front-side coating reduces reflections and improves the photolithographic contrast to the extent that it would enable the fabrication of arrays with smaller feature sizes. In one embodiment, by employing front-side coating with dielectric compounds, it is possible to manufacture an army of polymers with the size of a feature smaller than about 20 μm. In another embodiment, it is possible to manufacture an array of polymers with the size of a feature smaller than about 10, 5, 4, 2, 1 or 0.5 μm.

Dielectric coatings for optical applications are generally formed by vacuum evaporation, sputtering, or low-temperature solution deposition over suitable glass, ceramics, or metal substrate material. Such dielectric coatings may include materials with antireflective, index matching and/or light absorbing properties. The particular optical function and the wavelength or wavelengths of use for the optical coating dictates the coating design. Here the term coating design refers to the number of discrete layers of material to be deposited, the thickness of these layers and materials from which the layers are to be fabricated. The difference in refractive index between the materials that form the discrete layers is the physical property that, in combination with the coating design, gives the coating its unique function. For example, coatings can be designed to function as reflectors, anti-reflectors, polarizers, and other optical elements. In one embodiment, the dielectric coating is a low-reflectivity ultraviolet absorbing dielectric coating. In another embodiment, the coating is a dichroic antireflective coating. A dichroic antireflective coating is both antireflective and dichroic i.e., absorbing some wavelengths and transmitting others.

Antireflective coatings can range from a simple single layer having virtually zero reflectance at just one wavelength, to a multilayer system of more than a dozen layers, having virtually zero reflectance over a range of several octaves. The type used in any particular application will depend on a variety of factors, including the substrate material, the wavelength region, the required performance and the cost. In some cases, it may be desirable to use metal in one or more of the layers of the coating.

Very promising designs can be improved by computer refinement. The simplest form of antireflective coating is a single layer which has a limited number of adjustable parameters. Materials suitable for use as thin films are limited in number and the designer has to use what is available. An alternative embodiment is to use more layers, specifying obtainable refractive indices for all layers at the start, and to achieve zero reflectance by varying the thickness. Much of this design work is carried out by automatic methods. Automatic design techniques function more efficiently when they are furnished with good starting designs. One of skill in the art will be able to design and carry out the coatings according to specifications desired.

The fundamental specification of the antireflective layer is that the intensity of all sources of actinic backscattered light during photolithographic exposure must be no greater than the intensity of light directly transmitted through the chromium mask. Backscattered light includes all specular and diffuse reflection from the wafer coating and from the metal fixture to which the wafer is mounted on the exposure tool. The UV reflectance of the fixture may approach 100%.

In one preferred embodiment, the nominal photolysis wavelength is 365 nanometers. However, neither the absorption spectrum of the photolabile MeNPOC protecting groups nor the emission of the photolysis lamp is monochromatic. The 407 nm Hg emission line is measurably actinic, with roughly 7% of the total area of the action spectrum falling above 400 nm. Therefore the absorbance and reflectivity of the coating may be specified at both the 365 nm and 406 nm mercury emission wavelengths. Given the roughly 10-fold lower actinic power of the 406 nm line, the attenuation and reflectance specifications may be set proportionally lower than the 365 specifications. Also, some other photogroups and/or photoresist processes respond at wavelengths longer than 365 nm.

In another preferred embodiment, the optical density of the chromium layer on the photographic masks is approximately 3.5 across the near UV. In order to hold all sources of stray light below the transmitted intensity of the chromium, the single pass optical density and internal reflectance of the front-side antireflective coating may be specified, respectively, at 1.75 or greater and 0.0003 or less for the 365 nm wavelength and 1.25 or greater and 0.003 or less for the 406 nm wavelength.

In another preferred embodiment, general specifications for the front-side coating are set at greater than about 75% absorption in the "photo-reactive" UV wavelength region, less than about 40% absorbance in the visible wavelength region and less than about 10% reflectivity in the "photo-reactive" UV wavelength region. The higher the UV absorption is, the less back-reflected light will reach the synthesis surface, and the higher the contrast will be.

In further preferred embodiment, the coatings will have an outermost layer consisting of $SiO_2$, which provides a protective layer to stabilize the coating towards the harsh chemical conditions encountered during array manufacturing and also provides a surface that is chemically similar to the untreated fused silica substrates. The $SiO_2$ layer thus makes the surface suitable for chemical functionalization with the silanation reagents. The thickness of the $SiO_2$ is preferably between 50-1000 nm. In yet another preferred embodiment, the coatings will also have an outermost layer consisting of $SiO_x$ where x is a number or fractional number between O and 2.

In one preferred embodiment, the coatings will have an outermost layer consisting of a surface providing reactive functional groups, e.g., hydroxyl, carboxyl, amino, thiol, haloalkyl, 1,2-diol, aldehyde, acryloyl, maleimidyl, N-succinimidylcarboxylate groups or the like, to which the first monomers in the polymer sequence may be attached. This functionalized surface provides sites for synthesizing the various polymer sequences on that surface. See U.S. Pat. No. 5,959,098.

In contrast to the back-side coating, the front-side coating is left on the wafer permanently, because, unlike the back-side coating, it is intended to be very uniform and mostly transparent at the visible wavelengths used for scanning/detection.

In addition to improving the contrast, the front-side coating provides a "particle free" process thus increasing the confidence of maintaining a quality manufacturing operation.

IV. Silanation

Following coating of the substrate surface, the surface is derivatized to provide sites or functional groups on the substrate surface for synthesizing the various polymer sequences on that surface. In particular, derivatization provides reactive functional groups, e.g., hydroxyl, carboxyl, amino groups or the like, to which the first monomers in the polymer sequence may be attached. In one preferred aspect, the substrate surface is derivatized using silane in either water or ethanol. In another preferred aspect, the coated surface is derivatized by contacting the coated surface with a solution of silanation reagent. In further preferred aspect, the contacting of the surface of the substrate with silanation reagent is carried out by controlled vapor deposition of the silanation reagent on the surface.

Silanation reagents have been developed in the art which react with and coat surfaces, such as silica surfaces. For example, silanation reagents for use in modifying silica used in high performance chromatography packings have been developed. Monofunctional silanation reagents have been used to form monolayer surface coatings, while di- and tri-functional silanation reagents have been used to form polymerized coatings on silica surfaces. Many silanation reagents, however, produce coatings with undesirable properties including instability to hydrolysis and the inadequate ability to mask the silica surface which may contain residual acidic silanols. See U.S. Pat. No. 6,262,216 and U.S. Patent Application US2001/0021506A1.

Silanation reagents have been developed for the silylation of solid substrates, such as glass substrates, that include functional groups that may be derivatized by further covalent reaction. The silanation reagents have been immobilized on the surface of substrates, such as glass, and used to prepare high density immobilized oligonucleotide probe arrays. For example, N-(3-(triethoxysilyl)-propyl)-4-hydroxybutyramide (PCR Inc., Gainesville, Fla. and Gelest, Tullytown, Pa.) has been used to silylate a glass substrate prior to photochemical synthesis of arrays of oligonucleotides on the substrate, as described in McGall et al., *J. Am. Chem. Soc.*, 119:5081-5090 (1997), the disclosure of which is incorporated herein by reference.

Hydroxyalkylsilyl compounds that have been used to prepare hydroxyalkylated substances, such as glass substrates. N,N-bis(hydroxyethyl)aminopropyl-triethoxysilane has been used to treat glass substrates to permit the synthesis of high-density oligonucleotide arrays. McGall et al., *Proc. Natl. Acad. Sci.*, 93:13555-13560 (1996); and Pease et al., *Proc. Natl. Acad. Sci.*, 21:5022-5026 (1994), the disclosures of which are incorporated herein. Acetoxypropyl-triethoxysilane has been used to treat glass substrates to prepare them for oligonucleotide array synthesis, as described in PCT WO 97/39151, the disclosure of which is incorporated herein. 3-Glycidoxy propyltrimethoxysilane has been used to treat a glass substrate to provide a linker for the synthesis of oligonucleotides. EP Patent Application No. 89 120696.3.

Methods have been developed in the art for stabilizing surface bonded silicon compounds. The use of sterically hindered silanation reagents is described in Kirkland et al., *Anal. Chem.* 61: 2-11 (1989); and Schneider et al., *Synthesis*, 1027-1031 (1990). However, the use of these surface bonded silanation reagents is disadvantageous, because they typically require very forcing conditions to achieve bonding to the glass, since their hindered nature makes them less reactive with the substrate.

Additionally, silanes can be prepared having protected or "masked" hydroxyl groups and which possess significant volatility. As such, these silanes can be readily purified by, e.g., distillation, and can be readily employed in gas-phase deposition methods of silanating substrate surfaces. After coating these silanes onto the surface of the substrate, the hydroxyl groups may be deprotected with a brief chemical treatment, e.g., dilute acid or base, which will not attack the substrate-silane bond, so that the substrate can then be used for polymer synthesis. Examples of such silanes include acetoxyalkylsilanes, such as acetoxyethyltrichlorosilane, acetoxypropyltrimethoxysilane, which may be deprotected after application using, e.g., vapor phase ammonia and methylamine or liquid phase aqueous or ethanolic ammonia and alkylamines. Epoxyalkylsilanes may also be used, such as glycidoxypropyltrimethoxysilane which may be deprotected using, e.g., vapor phase HCl, trifluoroacetic acid or the like, or liquid phase dilute HCl.

The physical operation of silanation of the substrate generally involves dipping or otherwise immersing the substrate in the silane solution. Following immersion, the substrate is generally spun as described for the substrate stripping process, i.e., laterally, to provide a uniform distribution of the silane solution across the surface of the substrate. This ensures a more even distribution of reactive functional groups on the surface of the substrate. Following application of the silane layer, the silanated substrate may be baked to polymerize the silanes on the surface of the substrate and improve the reaction between the silane reagent and the substrate surface. Baking typically takes place at temperatures in the range of from 90° C. to 120° C. with 110° C. being most preferred, for a time period of from about 1 minute to about 10 minutes, with 5 minutes being preferred.

In alternative aspects, as noted above; silane may be contacted with the surface of the substrate using controlled vapor deposition methods or spray methods. These methods involve the volatilization or atomization of the silane solution into a gas phase or spray, followed by deposition of the gas phase or spray upon the surface of the substrate, usually by ambient exposure of the surface of the substrate to the gas phase or spray. Vapor deposition typically results in a more even application of the derivatization solution than simply immersing the substrate into the solution.

The efficacy of the derivatization process, e.g., the density and uniformity of functional groups on the substrate surface, may generally be assessed by adding a fluorophore which binds the reactive groups, e.g., a fluorescent phosphoramidite such as Fluoreprime™ from Pharmacia, Corp., Fluoredite™ from Millipore, Corp. or FAMT™ from ABI, and looking at the relative fluorescence across the surface of the substrate.

Figure 2:
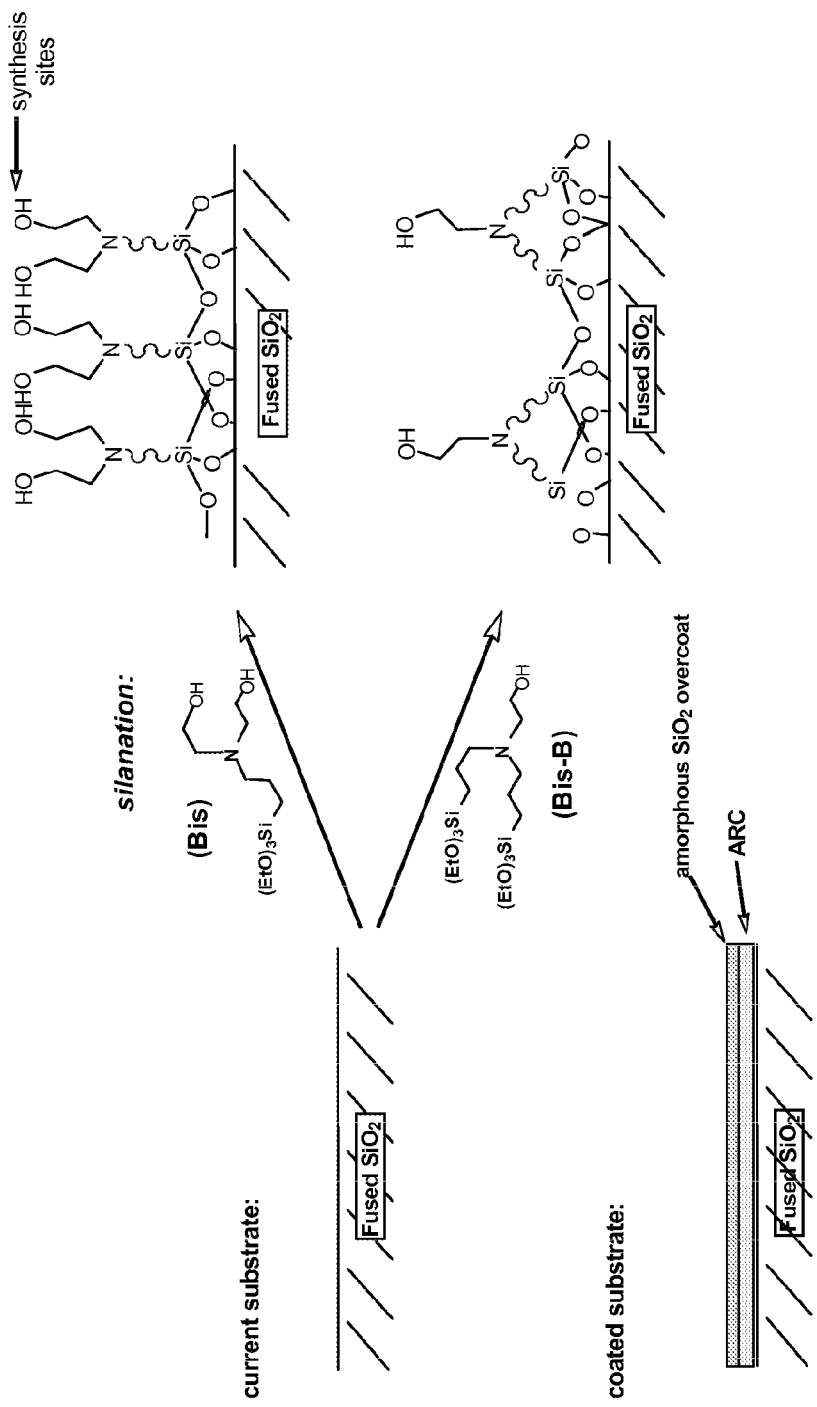
FIG. 2. Schematic diagrams showing attachment of Bis and Bis-B to fused silica.

In one preferred embodiment, Bis-hydroxyethyl-3-aminopropyltriethoxysilane (Bis) is used as the silanation reagent. In another preferred embodiment, N(2-hydroxyethyl)-N,N-bis(trimethoxysilylpropyl)amine (Bis-B) is used as the silanation reagent. Bis silane and Bis-B silane are bonded to fused silica as schematically shown in FIG. 2. Bis-B is more stable than B is as a result of its chemical structure, which provides two Si sites for attaching to fused silica compared to Bis with single Si sites.

BTMSE (Bis(trimethoxysilyl)-ethane) may be used to cross-link Bis silane coating to strengthen the surface bonding. In yet another preferred embodiment, Bis/BTMSE mixture is prepared by mixing Bis silane and BTMSE in varying proportions, wherein the mole percentage of Bis silane is preferably from 50% to 95%, more preferably from 75% to 95%, and most preferably from 80% to 90%.

In one embodiment, the silanation reagents may be covalently attached to the surface of a solid substrate to provide a coating comprising derivatizable functional groups on the substrate, thus permitting arrays of immobilized oligomers to be covalently attached to the substrate via covalent reaction with the reactive functional groups. The immobilized oligomers, such as polypeptides, or nucleic acids can be used in a variety of binding assays including biological binding assays. In another embodiment, high density arrays of immobilized nucleic acid probes may be formed on the substrate, and then one or more target nucleic acids comprising different target sequences may be screened for binding to the high density array of nucleic acid probes comprising a diversity of different potentially complementary probe sequences. For example, methods for light-directed synthesis of DNA arrays on glass substrates is described in McGall et al., *J. Am. Chem. Soc.*, 119:5081-5090 (1997), the disclosure of which is incorporated herein.

V. Photolysis Step

Photolithographic masks used during the photolysis step typically include transparent regions and opaque regions, for exposing only selected portions of the substrate during a given photolysis step. Typically, the masks are fabricated from glass that has been coated with a light-reflective or absorptive material, e.g., a chrome layer. The light-reflective or absorptive layer is etched to provide the transparent regions of the mask. These transparent regions correspond to the regions to be exposed on the surface of the substrate when light is shown through the mask.

As described above, photolithographic methods are used to activate selected regions on the surface of the substrate. Specifically, functional groups on the surface of the substrate or present on growing polymers on the surface of the substrate, are protected with photolabile protecting groups. Activation of selected regions of the substrate is carried out by exposing selected regions of the substrate surface to activation radiation, e.g., light within the effective wavelength range, as described previously. Selective exposure is typically carried out by shining a light source through a photolithographic mask. In one embodiment, the first layer of the substrate is derivatized and coated with functional groups protected with a photolabile protecting group. In a preferred embodiment, the photolabile protecting group is MeNPOC.

Because the individual feature sizes on the surface of the substrate prepared according to the processes described herein can typically range as low as 1-10 µm on a side, the effects of reflected or refracted light at the surface of the substrate can have significant effects upon the ability to expose and activate features of this size.

The light source used for photolysis is selected to provide a wavelength of light that is photolytic to the particular protecting groups used, but which will not damage the forming polymer sequences. Typically, a light source which produces light in the UV range of the spectrum will be used. For example, in oligonucleotide synthesis, the light source typically provides light having a wavelength above 340 nm, to effect photolysis of the photolabile protecting groups without damaging the forming oligonucleotides. This light source is generally provided by a Hg-Arc lamp employing a 340 nm cut-off filter (i.e., passing light having a wavelength greater than 340-350 nm). Typical photolysis exposures are carried out at from about 6 to about 10 times the exposed half-life of the protecting group used, with from 8-10 times the half-life being preferred. For example, MeNPOC, a preferred photolabile protecting group, has an exposed half-life of approximately 6 seconds, which translates to an exposure time of approximately 36 to 60 seconds.

VI. Chemistry Step

Following each photolysis step, a monomer building block is introduced or contacted with the synthesis surface of the substrate. Typically, the added monomer includes a single active functional group, for example, in the case of oligonucleotide synthesis, a 3'-hydroxyl group. The remaining functional group that is involved in linking the monomer within the polymer sequence, e.g., the 5'-hydroxyl group of a nucleotide, is generally photoprotected. The monomers then bind to the reactive moieties on the surface of the substrate, activated during the preceding photolysis step, or at the termini of linker molecules or polymers being synthesized on the substrate.

Typically, the chemistry step involves solid phase polymer synthesis methods that are well known in the art. For example, detailed descriptions of the procedures for solid phase synthesis of oligonucleotides by phosphoramidite, phosphite-triester, phosphotriester, and H-phosphonate chemistries are widely available. See, for example, Itakura, U.S. Pat. No. 4,401,796; Caruthers et al., U. S. Pat. Nos. 4,458,066 and 4,500,707; Beaucage et al., *Tetrahedron Lett.*, 22:1859-1862 (1981); Matteucci et al., *J. Amer. Chem. Soc.*, 103:3185-3191 (1981); Caruthers et al., *Genetic Engineering* 4:1-17 (1982); Jones, chapter 2, Atkinson et at, chapter 3, and Sproat et al., chapter 4, in Gait, ed. *Oligonucleotide Synthesis: A Practical Approach*, IRL Press, Washington D.C. (1984); Froehler et at, *Tetrahedron Lett.*, 27:469-472 (1986); Froehler et al., *Nucleic Acids Res.*, 14:5399-5407 (1986); Sinha et al. *Tetrahedron Lett.*, 24:5843-5846 (1983); and Sinha et al., *Nucl. Acids Res.*, 12:4539-4557 (1984).

Following overall synthesis of the desired polymers on the substrate wafers, permanent protecting groups, e.g., those which were not removed during each synthesis step, typically remain on nucleobases and the phosphate backbone of synthetic oligonucleotides. Removal of these protecting groups is usually accomplished with a concentrated solution of aqueous ammonium hydroxide. While this method is effective for the removal of the protecting groups, these conditions can also cleave the synthetic oligomers from the support by hydrolyzing an ester linkage between the oligo and a silane derivative that is bonded to the support. In oligonucleotide arrays, it is desirable to preserve the linkage connecting the oligonucleotides to the glass after the final deprotection step. Silanation reagents Bis, Bis-13 and Bis/BTMSE provide such stable linkage connecting the oligonucleotides to the glass.

VII. Applications

The methods and compositions disclosed herein may be used in a variety of applications. Substrates may be made having a first layer on a solid support including one or more dielectric coatings with antireflective materials and a second layer including biopolymers disposed on the first layer. In some embodiments, the substrate is substantially planar. In some embodiments, the substrate may be physically separated into regions, for example, with trenches, grooves, wells and the like. Examples of substrates include slides, beads and solid chips. The solid substrates may be, for example, biological, nonbiological, organic, inorganic, or a combination thereof, and may be in forms including particles, strands, gels, sheets, tubing, spheres, containers, capillaries, pads, slices, films, plates, and slides depending upon the intended use.

In one embodiment, high density arrays of immobilized nucleic acid probes may be formed on the substrate, and then one or more target nucleic acids comprising different target sequences may be screened for binding to the high density array of nucleic acid probes comprising a diversity of different potentially complementary probe sequences. For example, methods for light-directed synthesis of DNA arrays on glass substrates is described in McGall et al., *J. Am. Chem. Soc.*, 119:5081-5090 (1997), the disclosure of which is incorporated herein.

Methods for screening target molecules for specific binding to arrays of polymers, such as nucleic acids, immobilized on a solid substrate, are disclosed, for example, in U.S. Pat. No. 5,510,270, the disclosure of which is incorporated herein.

The fabrication of arrays of polymers, such as nucleic acids, on a solid substrate, and methods of use of the arrays in different assays, are also described in: U.S. Pat. Nos. 5,774,101, 5,677,195, 5,624,711, 5,599,695, 5,445,934, 5,451,683, 5,424,186, 5,412,087, 5,405,783, 5,384,261, 5,252,743 and 5,143,854; PCT WO 92/10092, the disclosures of each of which are incorporated herein. Accessing genetic information using high density DNA arrays is further described in Chee, *Science* 274:610-614 (1996), the disclosure of which is incorporated herein by reference, The combination of photolithographic and fabrication techniques allows each probe sequence to occupy a very small site on the support. The site may be as small as a few microns or even a small molecule. Such probe arrays may be of the type known as Very Large Scale Immobilized Polymer Synthesis (VLSIPS®) arrays, as described in U.S. Pat. No. 5,631,734, the disclosure of which is incorporated herein.

In the embodiment wherein arrays of nucleic acids are immobilized on a surface, the number of nucleic acid sequences may be selected for different applications, and may be, for example, about 100 or more, or, e.g., in some embodiments, more than $10^5$ or $10^8$. In one embodiment, the surface comprises at least 100 probe nucleic acids each preferably having a different sequence, each probe contained in an area of less than about 0.1 cm$^2$, or, for example, between about 1 um$^2$ and 10,000 um$^2$, and each probe nucleic acid having a defined sequence and location on the surface. In one embodiment, at least 1,000 different nucleic acids are provided on the surface, wherein each nucleic acid is contained within an area less than about $10^4$ cm$^2$, as described, for example, in U.S. Pat. No. 5,510,270, the disclosure of which is incorporated herein.

Arrays of nucleic acids for use in gene expression monitoring are described in PCT WO 97/10365, the disclosure of which is incorporated herein. In one embodiment, arrays of nucleic acid probes are immobilized on a surface, wherein the array comprises more than 100 different nucleic acids and wherein each different nucleic acid is localized in a predetermined area of the surface, and the density of the different nucleic acids is greater than about 60 different nucleic acids per 1 cm$^2$.

Arrays of nucleic acids immobilized on a surface which may be used also are described in detail in U.S. Pat. No. 5,744,305, the disclosure of which is incorporated herein. As disclosed therein, on a substrate, nucleic acids with different sequences are immobilized each in a predefined area on a surface. For example, 10, 50, 60, 100, $10^3$, $10^4$, $10^5$, $10^6$, $10^7$, or $10^8$ different monomer sequences may be provided on the substrate. The nucleic acids of a particular sequence are provided within a predefined region of a substrate, having a surface area, for example, of about 1 cm$^2$ to $10^{40}$ cm$^2$. In some embodiments, the regions have areas of less than about $10^{-1}$, $10^{-2}$, $10^{-3}$, $10^{-4}$, $10^{-5}$, $10^{-6}$, $10^{-7}$, $10^{-8}$, $10^{-9}$, or $10^{-10}$ cm$^2$. For example, in one embodiment, there is provided a planar, non-porous support having at least a first surface, and a plurality of different nucleic acids attached to the first surface at a density exceeding about 400 different nucleic acids/cm$^2$, wherein each of the different nucleic acids is attached to the surface of the solid support in a different predefined region, has a different determinable sequence, and is for example, at least 4 nucleotides in length. The nucleic acids may be, for example, about 4 to 20 nucleotides in length. The number of different nucleic acids may be, for example, 1000 or more. In the embodiment where polynucleotides of a known chemical sequence are synthesized at known locations on a substrate, and binding of a complementary nucleotide is detected; and wherein a fluorescent label is detected, detection may be implemented by directing light to relatively small and precisely known locations on the substrate. For example, the substrate is placed in a microscope detection apparatus for identification of locations where binding takes place. The microscope detection apparatus includes a monochromatic or polychromatic light source for directing light at the substrate, means for detecting fluoresced light from the substrate, and means for determining a location of the fluoresced light. The means for detecting light fluoresced on the substrate may in some embodiments include a photon counter. The means for determining a location of the fluoresced light may include an x/y translation table for the substrate. Translation of the substrate and data collection are recorded and managed by an appropriately programmed digital computer, as described in U.S. Pat. No. 5,510,270, the disclosure of which is incorporated herein.

Devices for concurrently processing multiple biological chip assays may be used as described in U.S. Pat. No. 5,545,531, the disclosure of which is incorporated herein. Methods and systems for detecting a labeled marker on a sample on a solid support, wherein the labeled material emits radiation at a wavelength that is different from the excitation wavelength, which radiation is collected by collection optics and imaged onto a detector which generates an image of the sample, are disclosed in U.S. Pat. No. 5,578,832, the disclosure of which is incorporated herein. These methods permit a highly sensitive and resolved image to be obtained at high speed. Methods and apparatus for detection of fluorescently labeled materials are further described in U.S. Pat. Nos. 5,631,734 and 5,324,633, the disclosures of which are incorporated herein.

The methods and compositions described herein may be used in a range of applications including biomedical and genetic research and clinical diagnostics. Arrays of polymers such as nucleic acids may be screened for specific binding to a target, such as a complementary nucleotide, for example, in screening studies for determination of binding affinity and in diagnostic assays. In one embodiment, sequencing of polynucleotides can be conducted, as disclosed in U.S. Pat. No. 5,547,839, the disclosure of which is incorporated herein. The nucleic acid arrays may be used in many other applications including detection of genetic diseases such as cystic fibrosis, diabetes, and acquired diseases such as cancer, as disclosed in U.S. patent application Ser. No. 08/143,312, the disclosure of which is incorporated herein. Genetic mutations may be detected by sequencing by hybridization. In one embodiment, genetic markers may be sequenced and mapped using Type-IIs restriction endonucleases as disclosed in U.S. Pat. No. 5,710,000, the disclosure of which is incorporated herein.

Other applications include chip based genotyping, species identification and phenotypic characterization, as described in U.S. patent application Ser. No. 08/797,812, filed Feb. 7, 1997, and U.S. application Ser. No. 08/629,031, filed Apr. 8, 1996, the disclosures of which are incorporated herein.

Gene expression may be monitored by hybridization of large numbers of mRNAs in parallel using high density arrays of nucleic acids in cells, such as in microorganisms such as yeast, as described in Lockhart et al., *Nature Biotechnology*, 14:1675-1680 (1996), the disclosure of which is incorporated herein. Bacterial transcript imaging by hybridization of total RNA to nucleic acid arrays may be conducted as described in Saizieu et al., *Nature Biotechnology*, 16:45-48 (1998), the disclosure of which is incorporated herein.

All publications cited herein are incorporated herein by reference in their entirety.

The invention will be further understood by the following non-limiting examples.

VIII. EXAMPLES

Example 1

Contrast Experiment

One back-side antireflective coated (ARC) and one front-side ARC wafers were compared to evaluate their photolithographic contrast. Oligonucleotides were synthesized using a new mask set, Dev-Val, which have minichips at different feature sizes within a chip. Chips were stained with Sybr Green and analyzed. FIG. 3(a) shows a magnified section of the 12 micron feature size minichip scanned at 1.5 micron Pixel Size, with spot size of 3 micron. FIG. 3(b) is a magnified bottom left section of FIG. 3(a). These Sybr Green stained images show that the front-side antireflective coated (ARC) wafers have lower background, improved contrast, and resolution compared to the back-side antireflective coated (ARC) wafers.

Example 2

Foreground to Background Contrast

Figure 4:
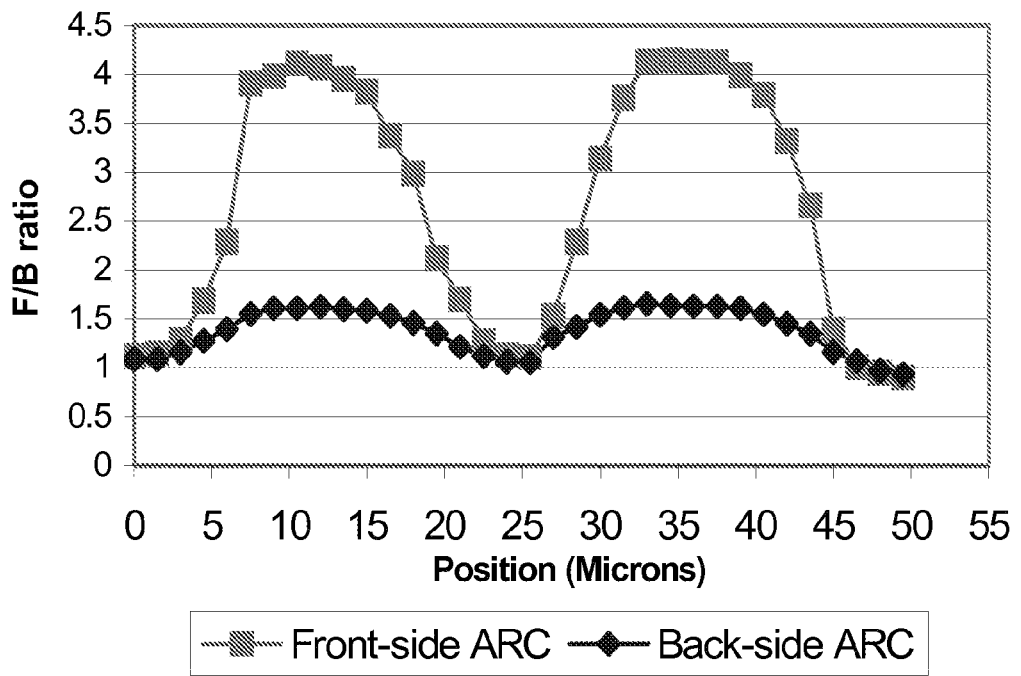
FIG. 4. Foreground to background contrast. Foreground to background contrast ratio of Sybr Green stained images of 12 micron feature size minichip scanned at 1.5 micron pixel size, Dev-Val Mask.

Sybr Green stain is used to evaluate contrast because it stains all DNA bases, allowing comparison between the intended synthesis (foreground) to areas where synthesis is not intended (Background). Foreground to background contrast ratio of Sybr Green stained images of 12 micron feature size minichip scanned at 1.5 micron pixel size, Dev-Val Mask is shown in FIG. 4. Results shows that contrast for the front-side ARC waver is 2.5 times higher than that of the back-side ARC wafers.

Example 3

Front-side ARC Vs Back-side ARC Wafers

Figure 5:
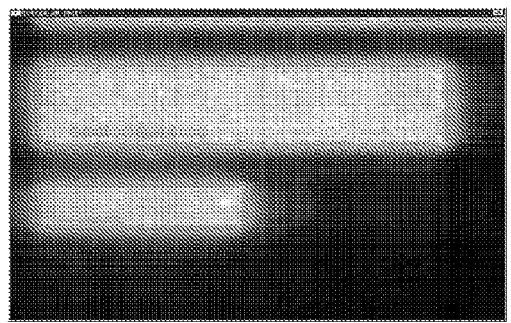
FIG. 5. Sybr-Green stained images: foreground to background contrast.
Figure 5:
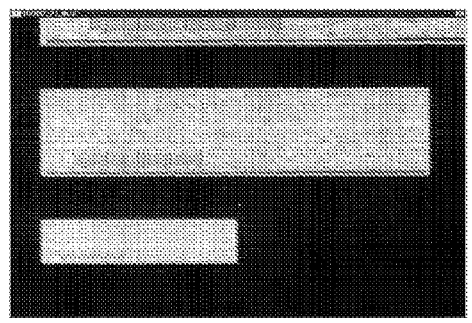
Figure 6:
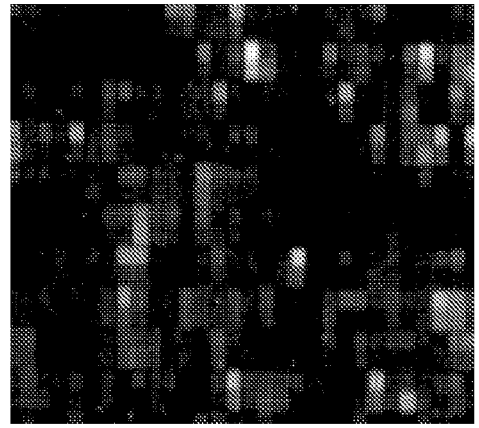
FIG. 6. Images of 20 micron feature probes of back-side ARC vs. front-side ARC chips.
Figure 6:
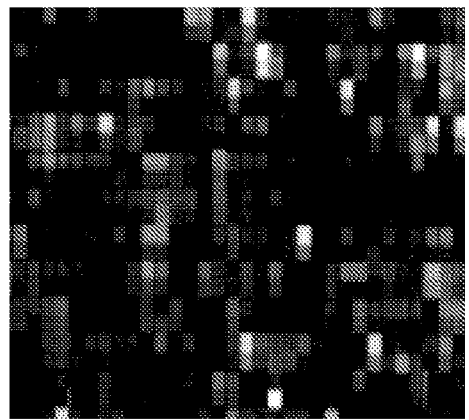

FIG. 5 shows the images of 20 micron features with the back-side versus the front-side ARC chips. In the left diagram, there are images of 2 and 1 micron minichips synthesized on the back-side ARC wafer. In the right diagram, the same images are processed with the front-side ARC wafer. Minichips are blocks of synthesized 25mer probes. The halo effect or the haze around the minichips indicates the light "noise" or edge effect. The reflected light is exposing the areas near the edge of the probes causing partial synthesis of unwanted probes. The front-side ARC chip shows a sharp crisp transition from the active to the non-active area indicating improved contrast.

Example 4

Front-side ARC Specification

The optical properties of the front-side ARC chips at several wavelengths will affect the overall product performance since the antireflective coating is on the front surface and is permanent. The MenPOC chemistry activates at 365 nm and 405 nm. The adhesive used to package the chips cures at 365 nm and 436 nm. The relative amount of light coming out of the mercury lamp produces approximately ⅓ of the energy at 365 nm and ⅔ of the energy at 436 nm.

The optical properties of the visible wavelengths at 488 nm, 530 nm and 570 nm are important since these are the wavelengths that the scanner reads the chips. The excitation wavelength of the scanner's argon-ion laser is 488. The fluorescein, Sybr Green detection wavelength is at 530 nm and the detection wavelength for phycoerythrin is at 570 nm. For the front-side ARC wafers, these visible wavelengths are attenuated and thus the fluorescence signal is reduced compared to a back-side ARC wafer where the antireflective coating is removed before being scanned. An example of desirable optical properties of the front-side ARC wafer is listed in the following table.

| Wavelength | % R | % T |
| --- | --- | --- |
| 365 | <5 | <5 |
| 405 | <5 | <30 |
| 436 | N/A | >30 |
| 488 | N/A | >60 |
| 530 | N/A | >70 |
| 570 | N/A | >70 |

Example 5

Surface Fluorescence Assay

It was shown, using a surface fluorescence assay that the intensity increase correlated with an increase in the hydrolytic stability of the silane coating in assay buffers. The pattern and intensity of surface fluorescence was imaged with a scanning laser confocal fluorescence microscope, which employed excitation with a 488 nm argon ion laser beam focused to a 2 micron spot size at the substrate surface. Emitted light was collected through confocal optics with a 530(+/−15) nm bandpass filter and detected with a PMT equipped with photon counting electronics. Output intensity values (photon counts/second) are proportional to the amount of surface-bound fluorescein, so that relative yields of free hydroxyl groups within different regions of the substrate could be determined by direct comparison of the observed surface fluorescence intensities. All intensity values were corrected for nonspecific background fluorescence, taken as the surface fluorescence within the non-illuminated regions of the substrate.

The relative surface reactive site density was measured. For each silicon compound tested, the number of available surface synthesis sites achieved per unit area was estimated by comparison of the observed initial surface fluorescence intensities of the various substrates immediately after deprotection in ethanolic diaminoethane.

$$\text{Site Density (\% rel.)} = \frac{\text{Intensity (tested silicon compound)} \times 100}{\text{Intensity (reference silicon compound)}}$$

To determine the relative stability of the silicon compound coatings, substrates were gently agitated on a rotary shaker at 45° C. in 5×SSPE aqueous buffer (BioWhittacker Products, Walkersville, Md.) at pH 7.3. Periodically, the substrates were removed from the buffer and re-scanned to measure the amount of fluorescein remaining bound to the surface.

It was shown that Bis-13 provides comparable or improved product performance compared to Bis silane as demonstrated by surface fluorescence assay.

What is claimed is:
1. A method of synthesizing an array of polymers, the method comprising:
   (a) providing a substrate, wherein a surface of the substrate comprises functional groups protected by photolabile protecting groups;
   (b) deprotecting the functional groups within selected regions of the surface, wherein deprotecting comprises illumination of the selected regions with light that is photolytic to the photolabile protecting groups, and wherein the selected regions correspond to locations on the surface where features of the array of polymers are synthesized;

(c) coupling monomers to the functional groups within the selected regions, wherein the monomers are protected by photolabile protecting groups; and (d) repeating steps (b)-(c) for one or more repetitions to synthesize the array of polymers, wherein steps (b)-(c) occur within a synthesis system, wherein the synthesis system comprises a light source and an anti-reflective coating, and wherein the anti-reflective coating reduces reflected illumination within the synthesis system such that the features of the array of polymers are smaller than 1 µm.

2. The method of claim 1, wherein the size of the features is smaller than 0.5 µm.

3. The method of claim 1, wherein the anti-reflective coating reflects less than about 10% of the light that is photolytic to the photolabile protecting groups.

4. The method of claim 3, wherein the anti-reflective coating reflects less than about 5% of the light that is photolytic to the photolabile protecting groups.

5. The method of claim 1, wherein the anti-reflective coating additionally possesses light absorbing properties.

6. The method of claim 1, wherein the anti-reflective coating has a transmittance of less than 5% for the light with a wavelength of 365 nm.

7. The method of claim 1, wherein the light includes one or more wavelengths longer than 340 nm.

8. The method of claim 1, wherein the light includes a wavelength of 365 nm.

9. The method of claim 1, wherein the synthesis system additionally comprises a flow cell.

10. The method of claim 9, wherein the synthesis system additionally comprises a fluid delivery system in fluid communication with the flow cell, wherein the fluid delivery system comprises a plurality of reagent reservoirs, and wherein the plurality of reagent reservoirs contain solutions with monomers for the array of polymers.

11. The method of claim 1, wherein at least one of the one or more repetitions utilizes a set of selected regions which is different from a previous set of selected regions.

12. The method of claim 1, wherein light including a wavelength of 365 nm is photolytic to the photolabile protecting groups.

13. The method of claim 12, wherein the photolabile protecting groups are MeNPOC.

14. The method of claim 1, wherein the array of polymers comprises polynucleotides.

15. The method of claim 1, wherein the array of polymers comprises polypeptides.

16. The method of claim 1, wherein the array of polymers comprises 1,000,000 different features.

17. The method of claim 1, wherein the substrate possesses two or more arrays of polymers.

18. The method of claim 1, wherein the substrate is about 1 inch by about 3 inches.

19. The method of claim 1, wherein the array of polymers occupies a portion of the substrate smaller than about 5 cm by about 5 cm.

20. A method of synthesizing an array of polymers, the method comprising:

(a) providing a substrate, wherein a surface of the substrate comprises functional groups protected by photolabile protecting groups;

(b) deprotecting the functional groups within selected regions of the surface, wherein deprotecting comprises illumination of the selected regions with light that is photolytic to the photolabile protecting groups, and wherein the selected regions correspond to locations on the surface where features of the array of polymers are synthesized;

(c) coupling monomers to the functional groups within the selected regions, wherein the monomers are protected by photolabile protecting groups; and (d) repeating steps (b)-(c) for one or more repetitions to synthesize the array of polymers, wherein steps (b)-(c) occur within a synthesis system, wherein the synthesis system comprises a light source and an anti-reflective coating, and wherein the anti-reflective coating reduces reflected illumination within the synthesis system such that the features of the array of polymers are smaller than 1 µm, wherein the anti-reflective coating absorbs greater than about 75% of the light that is photolytic to the photolabile protecting groups.

21. The method of claim 20, wherein the size of the features is smaller than 0.5 µm.

22. The method of claim 20, wherein the anti-reflective coating reflects less than about 10% of the light that is photolytic to the photolabile protecting groups.

23. The method of claim 20, wherein the anti-reflective coating reflects less than about 5% of the light that is photolytic to the photolabile protecting groups.

24. The method of claim 20, wherein the synthesis system additionally comprises a flow cell.

25. The method of claim 24, wherein the synthesis system additionally comprises a fluid delivery system in fluid communication with the flow cell, wherein the fluid delivery system comprises a plurality of reagent reservoirs, and wherein the plurality of reagent reservoirs contain solutions with monomers for the array of polymers.

26. The method of claim 20, wherein at least one of the one or more repetitions utilizes a set of selected regions which is different from a previous set of selected regions.

27. The method of claim 20, wherein light including a wavelength of 365 nm is photolytic to the photolabile protecting groups.

28. The method of claim 27, wherein the photolabile protecting groups are MeNPOC.

29. The method of claim 20, wherein the array of polymers comprises polynucleotides.

30. The method of claim 20, wherein the array of polymers comprises polypeptides.

31. The method of claim 20, wherein the array of polymers comprises 1,000,000 different features.

32. A method of synthesizing an array of polymers, the method comprising:

(a) providing a substrate, wherein a surface of the substrate comprises functional groups protected by photolabile protecting groups;

(b) deprotecting the functional groups within selected regions of the surface, wherein deprotecting comprises illumination of the selected regions with light that is photolytic to the photolabile protecting groups, and wherein the selected regions correspond to locations on the surface where features of the array of polymers are synthesized;

(c) coupling monomers to the functional groups within the selected regions, wherein the monomers are protected by photolabile protecting groups; and (d) repeating steps (b)-(c) for one or more repetitions to synthesize the array of polymers, wherein steps (b)-(c) occur within a synthesis system, wherein the synthesis system comprises a light source and an anti-reflective coating, and wherein the anti-reflective coating reduces reflected illumination within the synthesis system such that the features of the array of polymers are smaller than 0.5 μm.

33. A method of synthesizing an array of polymers, the method comprising:
  (a) providing a synthesis system and a substrate, wherein the synthesis system comprises a light source, a flow cell, a fluid delivery system in fluid communication with the flow cell, and an anti-reflective coating, wherein the substrate and the flow cell form a flow cell cavity, and wherein a surface of the substrate comprises functional groups protected by photolabile protecting groups;
  (b) deprotecting the functional groups within selected regions of the surface, wherein deprotecting comprises illumination of the selected regions with light that is photolytic to the photolabile protecting groups, wherein the light includes at least one wavelength above 340 nm, and wherein the selected regions correspond to locations on the surface where features of the array of polymers are synthesized;
  (c) coupling monomers to the functional groups within the selected regions, wherein the monomers are delivered to the flow cell cavity by the fluid delivery system, and wherein the monomers are protected by photolabile protecting groups; and
  (d) repeating steps (b)-(c) for one or more repetitions to synthesize the array of polymers, wherein the anti-reflective coating reduces reflected illumination from the light source within the synthesis system such that the features of the array of polymers are smaller than 1 μm.

* * * * *